(12) United States Patent
Kónya

(10) Patent No.: US 11,191,561 B2
(45) Date of Patent: Dec. 7, 2021

(54) ROTATABLE DECLOTTING APPARATUS AND METHOD

(71) Applicant: András Kónya, Sugar Land, TX (US)

(72) Inventor: András Kónya, Sugar Land, TX (US)

(73) Assignee: András Kónya, Sugarland, TX (US)

( * ) Notice: Subject to any disclaimer, the term of this patent is extended or adjusted under 35 U.S.C. 154(b) by 170 days.

(21) Appl. No.: 16/141,392

(22) Filed: Sep. 25, 2018

(65) Prior Publication Data

US 2019/0105074 A1   Apr. 11, 2019

Related U.S. Application Data

(60) Provisional application No. 62/568,474, filed on Oct. 5, 2017.

(51) Int. Cl.
*A61B 17/3207* (2006.01)
*A61B 17/221* (2006.01)
(Continued)

(52) U.S. Cl.
CPC ...... *A61B 17/32075* (2013.01); *A61B 17/221* (2013.01); *A61B 17/320725* (2013.01); *A61B 17/320758* (2013.01); *A61B 2017/0046* (2013.01); *A61B 2017/00398* (2013.01); *A61B 2017/00407* (2013.01); *A61B 2017/00862* (2013.01); *A61B 2017/00867* (2013.01);
(Continued)

(58) Field of Classification Search
CPC .... A61B 2017/2212; A61B 2017/2215; A61B 2017/2217; A61B 17/221; A61B 17/3207; A61B 17/320725; A61B 17/32075; A61B 17/320758; A61B 17/22038
See application file for complete search history.

(56) References Cited

U.S. PATENT DOCUMENTS 5,030,201 A * 7/1991 Palestrant ...... A61B 17/320725
604/22
5,634,679 A * 6/1997 Hilderbrandt ......... A47J 43/283
294/8

(Continued)

OTHER PUBLICATIONS

Akonya Eliminator, Thrombectomy Device, IDev Technologies, U.S. Pat. No. 6,146,396, Australian Patent No. 768224, Mar. 15, 2005.

*Primary Examiner* — Diane D Yabut
(74) *Attorney, Agent, or Firm* — Park, Vaughan, Fleming & Dowler LLP; Shane Nelson

(57) ABSTRACT

The present disclosure provides a method, system, and apparatus that adds rotational functionality to a conventional clot maceration device. The rotational functionality can be imparted by a wide variety of mechanical devices, such as by a hand operated rack and pinion type gear system or an electrically driven motor. An outer member (such as a catheter) of a declotting apparatus may be rotated while an inner member remains substantially fixed in position. The degree of rotation of the inner member may be between 60 and 180 degrees in a clockwise and counterclockwise rotation. In one embodiment, the rotating mechanism is coupled to a sliding and/or lateral mechanism to impart both lateral and rotational movement to the declotting apparatus. The deformable members of a basket or jacket of the declotting apparatus may form a helical structure and/or each comprise a bundled wire.

29 Claims, 10 Drawing Sheets

(51) Int. Cl.
    *A61B 17/22*      (2006.01)
    *A61B 17/00*      (2006.01)
    *A61B 17/29*      (2006.01)

(52) U.S. Cl.
    CPC ............ *A61B 2017/2215* (2013.01); *A61B 2017/22038* (2013.01); *A61B 2017/22082* (2013.01); *A61B 2017/22084* (2013.01); *A61B 2017/2916* (2013.01); *A61B 2017/2923* (2013.01)

(56) References Cited

U.S. PATENT DOCUMENTS

| | | | | |
|---|---|---|---|---|
| 6,146,396 A | * | 11/2000 | Konya | A61B 17/221 606/159 |
| 2002/0077631 A1 | * | 6/2002 | Lubbers | A61F 2/0811 606/232 |
| 2002/0143346 A1 | * | 10/2002 | McGuckin, Jr. | A61B 17/07207 606/139 |
| 2017/0224364 A1 | * | 8/2017 | Imai | A61B 17/320758 |

* cited by examiner

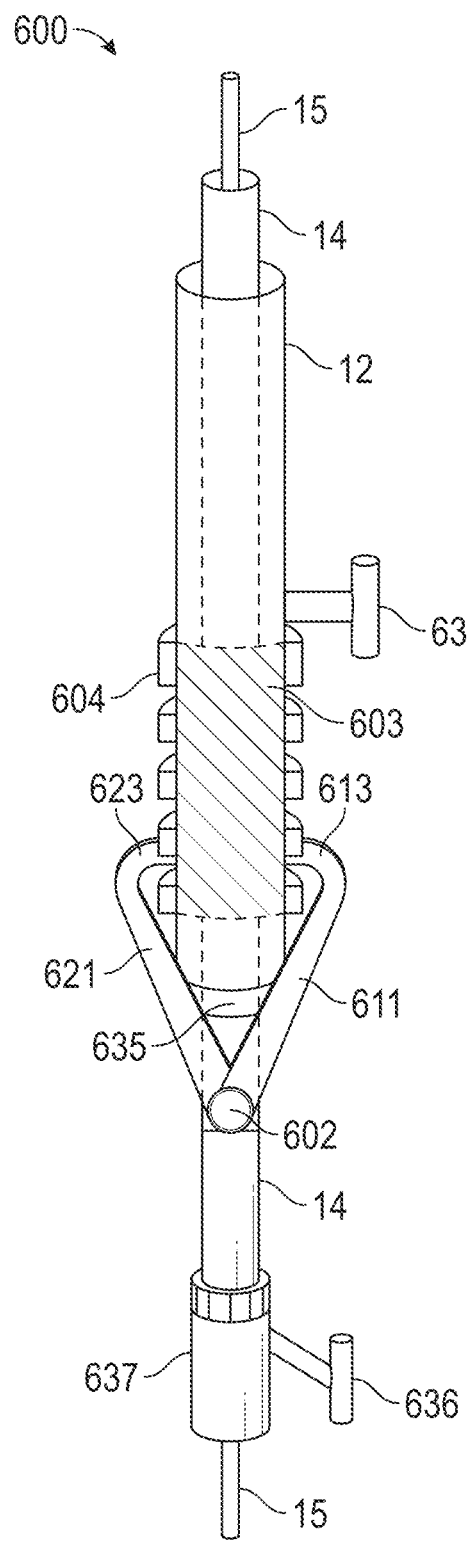
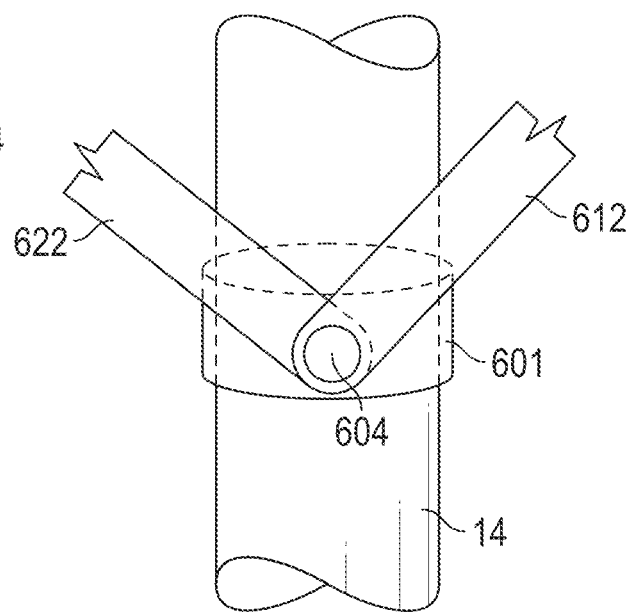
FIG. 6A
FIG. 6B

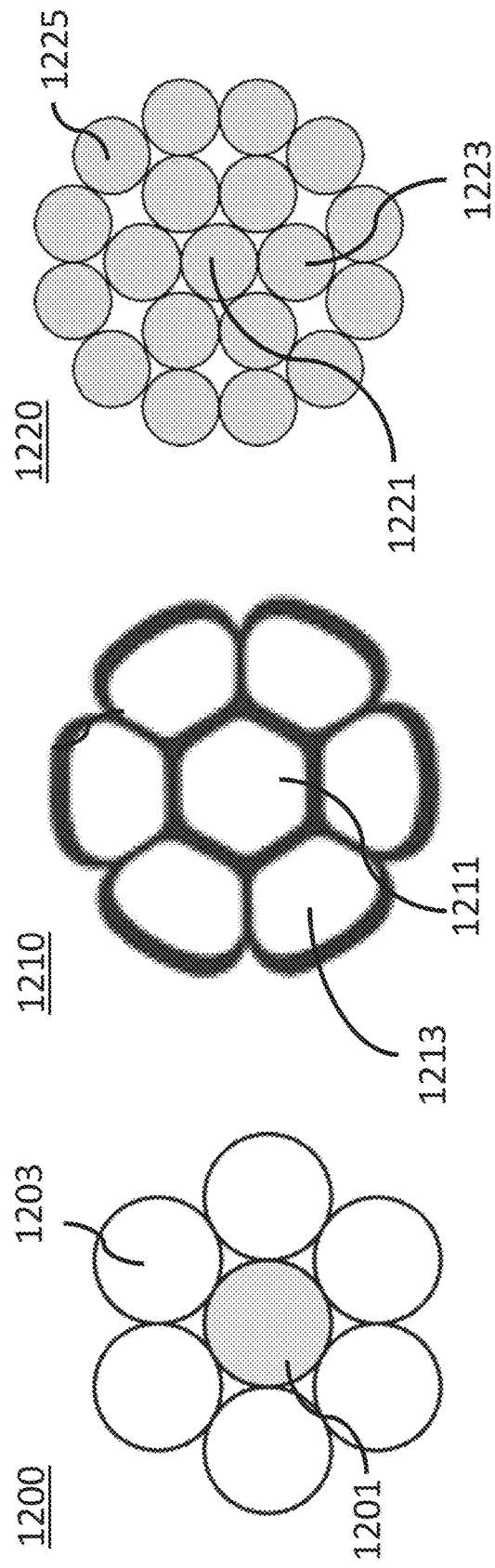

ROTATABLE DECLOTTING APPARATUS AND METHOD

PRIORITY

This application claims priority to U.S. provisional patent application no. 62/568,474, filed on Oct. 5, 2017, the entire contents of which is incorporated herein by reference.

BACKGROUND OF THE INVENTION

Field of the Invention

The invention relates to generally to the field of interventional radiology. More particularly, it concerns a method and apparatus for reconstructing a flow path within a vascular conduit, and even more particularly, it concerns embolectomy and thrombectomy, including treatment of thrombosed hemodialysis access grafts.

Description of the Related Art

Several devices have been used to perform mechanical thrombolysis. Some of these prior art devices are described in U.S. Pat. No. 6,146,396 ("the '396 patent"), incorporated herein by reference. The '396 patent describes one such device used to perform a mechanical thrombolysis, which describes general methods and apparatuses for declotting. In general, the declotting apparatus of the '396 patent includes a catheter, a member positioned within the catheter, and a plurality of deformable members that are used to remove a clot. FIG. 1 of the '396 patent is reproduced in the present disclosure as FIG. 1A as an exemplary declotting apparatus that may be used in conjunction with the present invention. As reproduced from the '396 patent:

> "Turning first to FIG. 1, there is shown a declotting apparatus 10 according to one embodiment of the presently disclosed method and apparatus. Apparatus 10 includes a catheter 12, a member 14, and a deformable jacket 16. Jacket 16 has a proximal end 18 and a distal end 20. The proximal end is coupled to catheter 12 at proximal site 22. Distal end 20 is coupled to member 14 at distal site 24. As illustrated, proximal site 22 and distal site 24 may be separated by a distance. In operation, the distance between proximal site 22 and distal site 24 may be changed by sliding catheter 12 relative to member 14 so that deformable jacket 16 becomes expanded or contracted. It is to be understood that in other embodiments, member 14 may be moved relative to catheter 12 so as to achieve a similar effect upon deformable jacket 16. The expansion of deformable jacket 16 allows for the maceration of clots and for the declotting of a site, including, but not limited to a vascular stenosis, or a thrombosed hemodialysis polytetrafluroethylene (PTFE) graft site."

FIG. 4 of the '396 patent is reproduced in the present disclosure as FIG. 1B as another exemplary declotting apparatus that may be used in conjunction with the present invention. The embodiment described in FIG. 1B differs from the embodiment described in FIG. 1A primarily in that rather than using a deformable jacket/basket (as in FIG. 1A), a plurality of deformable members 30 (such as individual wire members) are used. As reproduced from the '396 patent:

> "Turning now to FIG. 4, there is shown a declotting apparatus 10 that includes a catheter 12, a member 14, a plurality of deformable members 30, a proximal portion 22, a distal portion 24, a guidewire 15 having an angled portion 17, and a pair of clips 32. The operation of the embodiment illustrated in FIG. 4 is similar to that of the embodiments illustrated in FIG. 1, FIG. 2 and FIG. 3 in that the distance between proximal portion 22 and distal portion 24 may be modified so as to expand or contract the plurality of deformable members 30. More particularly, the distance may be modified to bow the plurality of deformable members 30 as the distance is reduced, and to compress the plurality of deformable members 30 as the distance is increased. The distance between proximal portion 22 and distal portion 24 may be changed by sliding catheter 12 relative to member 14 (or vice versa)."

FIG. 7 of the '396 patent is reproduced in the present disclosure as FIG. 1C as another exemplary declotting apparatus that may be used in conjunction with the present invention. The embodiment described in FIG. 1C differs from the embodiments in FIGS. 1A and 1B primarily based on the inclusion of a "sliding agent" to slide the catheter relative to the member in a lateral direction. As reproduced from the '396 patent:

> "Turning to FIG. 7 there is shown a declotting apparatus 10 that includes a catheter 12, a member 14, a guide 26, a proximal site 22, distal site 24, a plurality of deformable members 30, a sliding agent 40, an injection port 50, and an injector 52."

> "The embodiment of FIG. 7 is similar to the embodiments described previously, but in FIG. 7 it is demonstrated that a sliding agent 40 may be designed so as to slide catheter 12 relative to member 14. In the illustrated embodiment, sliding agent 40 includes hand grip 42, one-arm lever 44, spring 46, and attachment site 48. In operation, reducing the angle between one-arm lever 44 and hand grip 42 may move catheter 12 relative to member 14. More specifically, pressing one-arm lever 44 may move catheter 12 distally (i.e. towards distal site 24). Although here illustrated as utilizing a one-arm lever and hand grip, those having skill in the art will understand, with the benefit of the present disclosure, that sliding agent 40 may be configured in any number of suitable alternative manners. For instance, sliding agent 40 may include a single handle coupled to, for instance, catheter 12. Such a handle may allow for, for example, the direct sliding of catheter 12 relative to member 14. In one embodiment, one-arm lever 44 or any suitable alternative structure may be equipped with a lock mechanism that secures any possible position of catheter 12 relative to member 14 continuously without using any determined increments."

> "In one embodiment, spring 46 is a stainless steel spring and is connected to the proximal end of catheter 12, which may be a 4-F Teflon catheter. Spring 46 may pull the 4-F Teflon catheter back and, as a result of traction, the plurality of deformable members 30, which may be nitinol wires, may be stretched completely into a fully contracted state. The proximal end of the catheter/wire system may be equipped with a locking mechanism that keeps the deformable members 30 in a fully contracted state. After unlocking such a mechanism, continuous sliding movement between proximal site 22 and distal site 24 may be carried out by the one-armed lever mechanism illustrated, which may produce the movement of the 4-F Teflon catheter over second member 14, which may be a nitinol wire or another catheter, such as a Teflon catheter. Releasing lever 44, spring 46 may retract catheter 12 resulting in a small profile of the plurality of deformable members 30. It will be understood that although the above embodiment was described with relation to an embodiment utilizing deformable members 30 without a deformable jacket, the description applies equally well for all the other embodiments described herein."

While conventional mechanical declotting apparatuses (such as that disclosed in the '396 patent) are useful in numerous instances, in certain applications they are not fast or effective as they need to be during removal of clots, such as when a clot is firmly attached to a vessel or graft wall or when a massive thrombus is treated. Further, while the declotting apparatuses described in the '396 patent offered significant advantages over other prior art declotting apparatuses, the '396 patent declotting apparatuses do not provide any rotation capabilities for the declotting apparatus.

The statements in this section are intended to provide background information related to the invention disclosed and claimed herein. Such information may or may not constitute prior art. It will be appreciated from the foregoing, however, that there remains a need for an improved method and system for clot macerations. A need exists for an improved method and system for rotating conventional declotting apparatuses during percutaneous intervention. Such disadvantages and others inherent in the prior art are addressed by various aspects and embodiments of the subject invention.

SUMMARY OF THE INVENTION

The present disclosure provides a method, system, and apparatus that adds rotational functionality to a conventional clot maceration device. The rotational functionality can be imparted by a wide variety of mechanical means, such as by a hand operated rack and pinion type gear system or an electrically driven motor. An outer member (such as a catheter) of a declotting apparatus may be rotated while an inner member remains substantially fixed in position. The degree of rotation of the outer member may be between 60 and 180 degrees in a clockwise and counterclockwise rotation, and in one embodiment pressing and releasing a handle causes the rotation mechanism to rotate back and forth in opposing directions. In one embodiment, the rotating mechanism is coupled to a sliding and/or lateral mechanism to impart both lateral and rotational movement to portions of the declotting apparatus at the same time. The deformable members of a basket or jacket of the declotting apparatus may form a helical structure and/or each comprise a bundled wire.

In one embodiment, a declotting apparatus is disclosed that comprises an outer member, an inner member positioned within said outer member, wherein the inner member is configured to be fixed in position relative to the outer member, a plurality of deformable members coupled to the inner member and the outer member, and a rotational device configured to rotate the outer member.

In another embodiment, a declotting apparatus is disclosed that comprises an outer member, an inner member positioned within said outer member, a plurality of deformable members coupled to the inner member and the outer member, and a rotational device configured to rotate the outer member or inner member.

In another embodiment, a rotational device for a declotting apparatus is disclosed that comprises a handle assembly configured to couple to a declotting apparatus, wherein the declotting apparatus comprises a catheter and an inner member, a spring coupled to the handle assembly, and a gear mechanism coupled to the handle assembly and catheter, wherein the handle assembly is configured to actuate the gear mechanism to rotate the catheter relative to the inner member.

In one embodiment, a method for declotting a site is disclosed that comprises providing a declotter, positioning the declotter adjacent the site, and rotating a plurality of deformable members of the declotter to declot the site. The declotter may comprise a catheter, a member positioned within the catheter, and a plurality of deformable members coupled to the catheter and the member.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A and 6B illustrate another embodiment of a locking mechanism for the disclosed rotating declotting apparatus.

FIGS. 12A-12E illustrate various schematics of wire bundles according to one embodiment of the present disclosure.

DETAILED DESCRIPTION

Figure 1C:
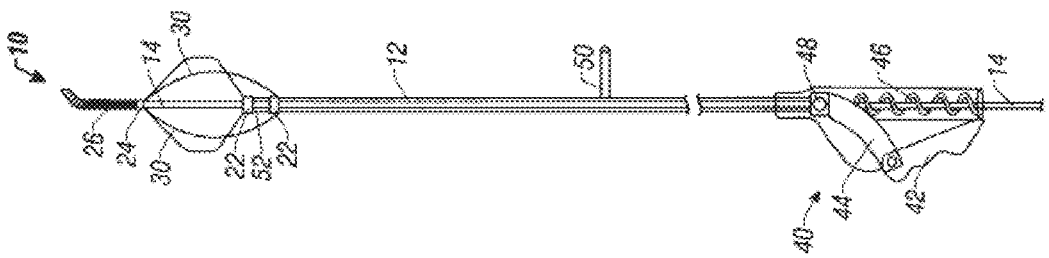
FIG. 1C illustrates one prior art declotting apparatus, which is taken from FIG. 7 of U.S. Pat. No. 6,146,396.

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure. The following detailed description does not limit the invention.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

The disclosed methods and apparatus allow for effective general declotting applications, clot maceration, removal of an arterial plug, and/or the reduction or elimination of intragraft thrombosis(es). In one aspect, the present disclosure is a declotting apparatus including a catheter, a member, and a plurality of deformable members. The deformable members may be positioned within the catheter and slidable relative to the catheter. The plurality of deformable members may form at least one loop and have a proximal portion and a distal portion. The proximal portion may be coupled to an outer member (such as a catheter) at a proximal site, and the distal portion may be coupled to an inner member at a distal site. In one embodiment, the plurality of deformable members is configured to bow as the catheter slides to reduce a distance between the proximal and distal portions and are configured to compress as the catheter slides to increase the distance. Its compact design, in one embodiment, provides controllable resistance and lets an operator better feel the apparatus during a given procedure. Because the disclosed apparatus may be flexible, it may be used with any suitable access shaft. Due in part to its low profile, the apparatus does not require large access sheaths, although large access sheaths may be used if desired. The general use of a similar declotting apparatus (and variations thereof) is described in U.S. Pat. No. 6,146,396, incorporated herein by reference.

The present disclosure adds a rotating mechanism to a conventional declotting apparatus that is operable to rotate the whole declotting apparatus or a portion of the declotting apparatus to facilitate removal of the clot. For example, a first portion (such as an inner member) may be rotated within a second portion (such as an outer member or catheter). The rotating mechanism may or may not be actuated by a handle mechanism, and in some embodiments may comprise or be coupled to an electric motor. In one embodiment, where the declotting apparatus as a whole is rotated, the degree of rotation may be 180 degrees in each direction. When only a part of the declotting apparatus is rotated, the degree of rotation of the inner member may be between 60 and 180 degrees in a clockwise and counterclockwise rotation. In one embodiment, pressing and releasing a handle causes the rotation mechanism to rotate back and forth in opposing directions. In one embodiment, the rotating mechanism is coupled to a sliding and/or axial mechanism to impart both axial and rotational movement to portions of the declotting apparatus at the same time. Thus, as compared to prior art declotting apparatuses, the disclosed declotting apparatus further comprises a rotating agent or device that is in operable relation to the catheter and/or inner member. In one embodiment, the catheter and inner member are fixed to each other and the whole device is rotated, while in other embodiments the catheter and inner member are not fixed together and the inner member is rotated within the catheter or vice versa when the catheter is rotated around the inner member. Such an apparatus provides for significant benefits, including faster and more efficacious declotting procedures, particularly when an adherent clot is present that is firmly attached to the vessel/graft wall. Further, the disclosed amount and speed of rotation can be easily varied based on the particular needs of the surgery and/or operator.

Figure 1B:
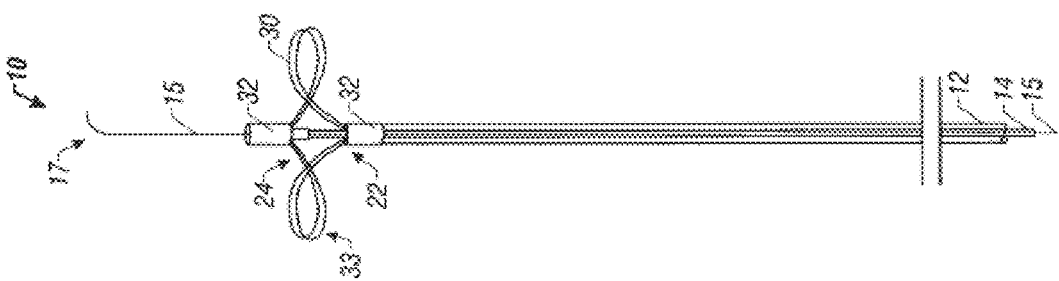
FIG. 1B illustrates one prior art declotting apparatus, which is taken from FIG. 4 of U.S. Pat. No. 6,146,396.
Figure 1A:
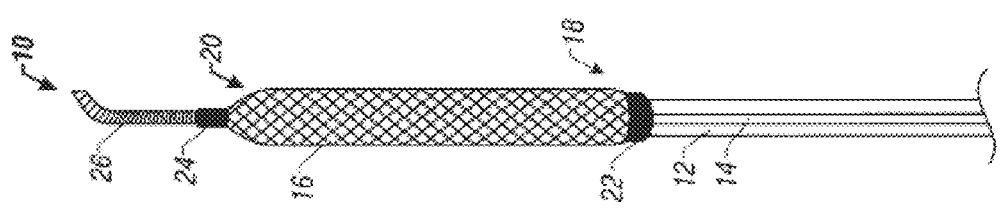
FIG. 1A illustrates one prior art declotting apparatus, which is taken from FIG. 1 of U.S. Pat. No. 6,146,396.
Figure 2A:
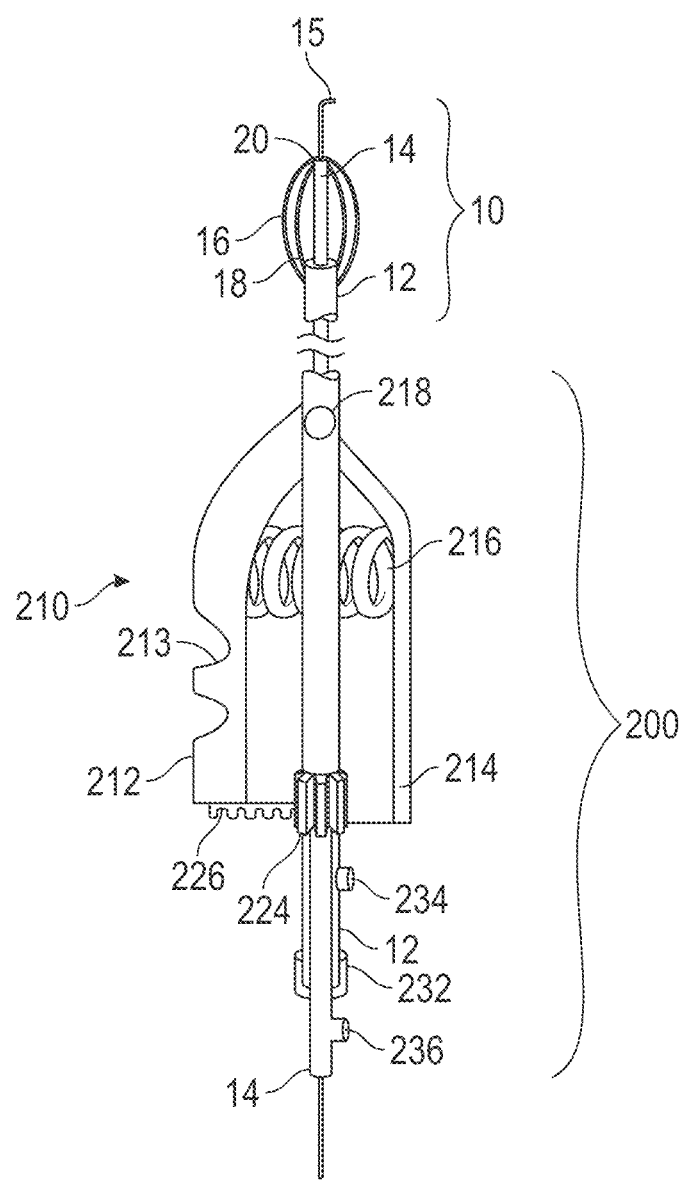
FIG. 2A illustrates one schematic of a rotational device for a declotting apparatus according to one embodiment of the present disclosure.
Figure 2B:
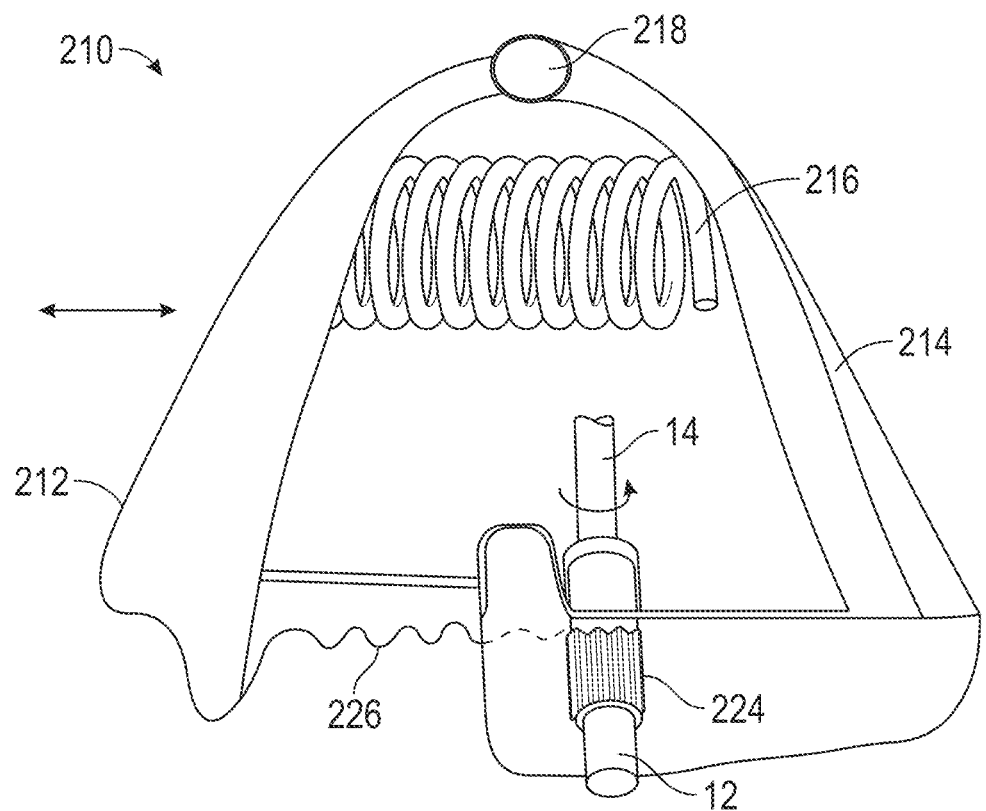
FIG. 2B illustrates an enlarged view of the handle assembly from FIG. 2A.
Figure 2C:
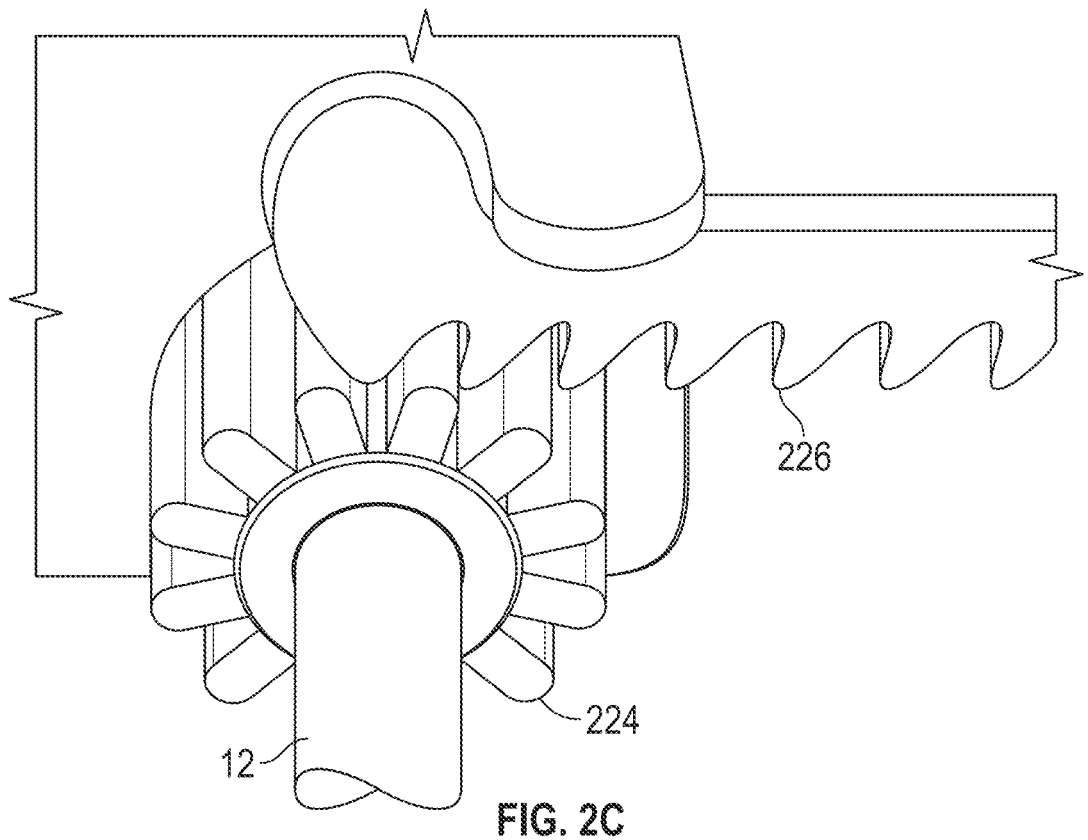
FIG. 2C illustrates an enlarged view of the rotating gear assembly from FIG. 2A.

FIGS. 2A-2C illustrate one schematic of a rotational device for a declotting apparatus according to one embodiment of the present disclosure. The embodiment disclosed in FIG. 2A allows for 180 degrees back and forth rotation (e.g., clockwise and counterclockwise) of the declotting apparatus. In one embodiment, the utilized declotting apparatus may be any number of the basic declotting apparatuses disclosed in U.S. Pat. No. 6,146,396, as well as any number of other declotting apparatuses with an inner and outer member. A portion of an exemplary declotting apparatus is described in FIG. 2A. For example, declotting apparatus 10 may comprise outer member 12 (e.g., a catheter), inner member 14, deformable jacket/basket 16, and guidewire 15 (with or without an angled portion of the guidewire). Jacket 16 has proximal end 18 and a distal end 20. The proximal end is coupled to catheter 12 at a proximal site, and distal end 20 is coupled to inner member 14 at a distal site. The proximal site and distal site may be separated by a certain distance which may be varied by sliding catheter 12 relative to member 14 so that deformable jacket 16 becomes expanded or contracted. Such a declotting apparatus is substantially similar to the declotting apparatuses disclosed in U.S. Pat. No. 6,146,396, a few embodiments which are reproduced in FIGS. 1A, 1B, and 1C of the present disclosure.

A plurality of deformable members may form and/or be part of deformable jacket/basket 16. In one embodiment, the deformable members may be created of nitinol, which can be programmed by heat treatment into preformed shapes, such as that described in U.S. Patent Publication No. 2006/0155303, incorporated herein by reference. In one embodiment, the deformable members are made of elastically deformable members, such as nitinol wires, that may be programmed with superelasticity or thermal memory. In particular, they may be programmed to substantially recover an arcuate shape upon removal of a compressing force. Programming of superelasticity or thermal memory may be accomplished by any one of a number of techniques known in the art, such as by first forming a desired arcuate shape. In a further possible embodiment, the deformable members are made of platinum cored microtubes. The platinum content increases the radiopacity of the device that in turn increases its visibility under fluoroscopy (X-ray) during a procedure. In short, better visibility translates to safety, efficacy, and speediness of the procedure. In a further embodiment, the individual single nitinol wires can be replaced with bundled wires (e.g., a set of individual wires coupled together), as described in more detail in relation to FIGS. 12A-12E.

As FIG. 2A illustrates, in one embodiment, rotating device 200 is coupled to a portion of declotting apparatus 10, such as proximal to basket 16. In one embodiment, rotating device 200 is coupled to either the inner or outer member of the declotting apparatus at a predetermined distance away from the deformable jacket/basket such that the rotating device may be operable during surgery. In one embodiment, rotating device 200 may comprise handle 210 attached to an outer member of a declotting apparatus, such as catheter/member 12. Handle 210 may have or be coupled to hand grip 212, spring 216, pivot 218, pinion 224, and rack 226. In one embodiment, pinion 224 is a round gear and/or cogwheel, and rack 226 may be straight or flat. Handle 210 may take any number of forms suitable for gripping with a hand, and may include various contours or recesses 213 suitable for gripping by one or more fingers. The handle may be substantially in the form of an elongated shape (much like the handle of a knife) or an oblong shape with rounded corners. In one embodiment, pinion 224 is coupled to outer portion 12 (e.g., a catheter) of the declotting apparatus, and rack 226 couples handle 210 to pinion 224. The interaction of pinion 224 and rack 226 acts much like a typical rack and pinion system. Thus, actuation of handle 212 engages rack 226 against pinion 224, thereby rotating pinion 224 and any portions of the declotting apparatus that are rigidly secured and/or fixed to the pinion. In one embodiment, the 180 degrees of rotation is achievable in this arrangement because pinion 224 has 12 teeth and rack 226 has 6 teeth, and the rack may allow half a circle revolution (e.g., a 180 degrees revolution) in a clockwise and anticlockwise direction. One of skill in the art will realize that many other rotational systems are also possible, such as those disclosed in FIGS. 7-10 (discussed later).

In one embodiment as seen in FIG. 2B, handle 210 may comprise spring 216 that connects portions of the handle together. For example, handle 210 may comprise first portion 212 (such as grip 212) and second portion 214, such that spring 216 couples first portion 212 to second portion 214 and allows the first and second portions of the handle to move relative to each other. In an embodiment, first portion 212 is configured to move while second portion 214 is configured to remain fixed in position. In one embodiment, first handle portion 212 rotates around a fixed point, such as pivot 218, and actuation of a first portion of the handle (such as grip 212) causes spring 216 to compress and the first handle portion to rotate around pivot 218.

FIGS. 2B and 2C illustrate enlarged schematics of different components of handle 210 from FIG. 2A. FIG. 2B shows one embodiment of the action mechanism of handle 210, while FIG. 2C shows one embodiment of the rotating gear assembly (e.g., pinion and rack) of FIG. 2A. In one embodiment, when an operator presses hand grip 212, a portion of rack 226 engages and/or moves over a portion of pinion 224. Because a member of the declotting apparatus is rigidly attached (such as catheter/member 12) to pinion 224, movement of the pinion will rotate a predefined distance, such as 180-degree counter clockwise. By selecting the size of the pinion, as well as the number of cogs (teeth) in the pinion in relation to the number of cogs (teeth) of the rack, varying degrees of rotation may be achieved. For example, if the pinion has 12 teeth and the rack is limited to 6 teeth, one actuation of the mechanism will result in 180 degrees of counter clockwise movement. By having a 1:1 ratio (e.g., the pinion and rack both have six teeth), the same actuation will give rise to 360 degrees of counter clockwise rotation. In one embodiment, grip handle 212 can produce a linear movement of about 20-30 mm. For example, if a rack has 24 teeth and the pinion has 6 teeth, the maximum number of rotations is 4, and if a rack has 24 teeth and the pinion has 4 teeth, the maximum number of rotations is 6. In one embodiment where the device rotates as a whole (e.g., catheter 12 and inner member 14 are secured together) a ratio of the teeth on the pinion and the rack, respectively, can be created to allow for rotational movement in a range of 180 degrees and up to 6 revolutions. In one embodiment, when the operator releases hand grip 212, spring 216 pushes and/or extends hand grip 212 back into the original position, which thereby moves rack 226 in an opposition direction, which thereby rotates pinion 224 and the attached member in an opposite movement. Thus, when the operator presses and releases hand grip 212 repeatedly, a back-and-forth (or clockwise and counterclockwise) rotation on member 12 will rotate a separate portion of the declotting apparatus, such as deformable jacket/basket 16. In a preferred embodiment, for basket 16 to rotate back and forth, members 12 and 14 should be locked relative to each other, such as by locking/valve mechanism 232 (see FIG. 2A). Such a back- and forth rotation mechanism, with between one to six full rotations at a time, will increase the clot maceration capability of the declotting device resulting in faster and more efficacious procedure than use of a declotting apparatus without rotational ability, particularly when an adherent clot is present that is firmly attached to the vessel/graft wall. This is a significant advantage over the prior art.

In one embodiment, member 12 can be fixed in position relative to member 14 by using different locking mechanisms. Referring to FIG. 2A, in one embodiment, rotating device 200 may have or be coupled to locking mechanism/valve 232, which may be located at a proximal end of member 12, which may be located on the declotting apparatus proximal to handle 210. Locking mechanism/valve 232 is configured to secure the positions of first member 12 and second members 14 relative to each other. In one embodiment, the locking mechanism may be a flexible valve that prevents blood from entering the catheter but also creates friction between the inner member and the valve itself that keeps catheter 12 and inner member 14 in position. In some embodiments, each of first member 12 and second member 14 may have a small profile side port 234, 236, respectively, for flushing the catheters with heparinized saline to remove air and blood and prevent intra-catheter coagulation. The side port can also be used to inject thrombolytic agents into the vessel to facilitate clot dissolving. In such an embodiment, the pure mechanical thrombectomy is effectively a pharmaco-mechanical thrombectomy. Such side ports are configured not to impede free rotation of members 12 and 14. In other embodiments, the locking mechanism may be a tightening screw mechanism (with or without a valve) attached to the proximal end of catheter 12, which can fix the spatial relationship between the two catheters. In another embodiment, the locking mechanism may comprise a thumb button that secures the two members together, which may be attached to the proximal end of catheter 12. For example, a thumb button may be coupled to a ratchet mechanism so as to lock members 12 and 14 relative to each other, similar to the embodiment described in FIGS. 9A and 9B of U.S. Pat. No. 6,146,396, incorporated herein by reference. In one embodiment, the declotter may be expanded, or "activated," by pushing a thumb-button coupled to the grip body and to the outer surface of catheter 12 distally. As a result, the working profile of declotter may increase in diameter. In one embodiment, a thumb-button may be fixed at certain points by a ratchet mechanism of the locking mechanism. Other locking mechanisms are described in relation to FIGS. 5A, 5B, 6A, and 6B.

Figure 3:
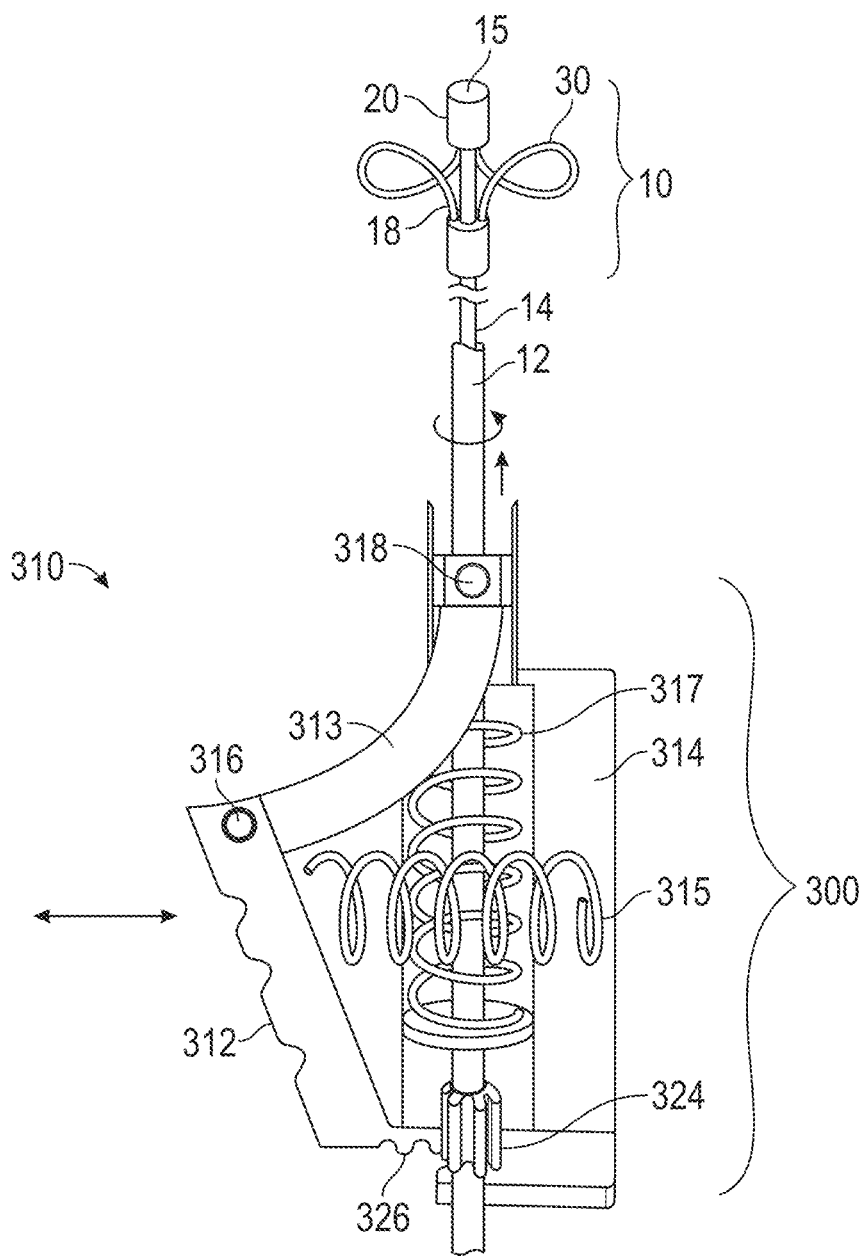
FIG. 3 illustrates one schematic of a rotational device for a declotting apparatus according to another embodiment of the present disclosure.

FIG. 3 illustrates one schematic of a rotational device for a declotting apparatus according to another embodiment of the present disclosure. This embodiment rotates only a portion of the declotting apparatus (such as catheter/outer member 12 as it is connected to pinion 324). The embodiment described in relation to FIG. 3 allows for a maximum of 180 degrees back and forth rotation (similar to the embodiment of FIG. 2A), but also allows for simultaneously increased/decreased diameter of the declotting apparatus basket. One embodiment combines the mechanisms of two separate handles, such as one handle that allows for increased diameter of the declotting basket (similar to the FIG. 7 embodiment described in the '396 patent and referenced here as FIG. 1C) and one handle (such as described above in relation to FIG. 2A) that can create a maximum 180-degree back and forth rotation of the basket.

FIG. 3 shows rotating device assembly 300 that allows for rotational and lateral/axial movement of one or more members of a declotting apparatus. In this embodiment, proximal ends of members 12 and 14 are not locked. Instead, they are able to move freely relatively to each other. In one embodiment, the utilized declotting apparatus may be any number of the declotting apparatuses disclosed in U.S. Pat. No. 6,146,396, as well as any number of other declotting apparatuses with an inner and outer member. A portion of an exemplary declotting apparatus is described in FIG. 3. For example, the declotting apparatus 10 may comprise an outer member 12 (e.g., a catheter), inner member 14, and deformable members 30, as well as guidewire 15. Deformable members 30 have a proximal end 18 and a distal end 20. The proximal end is coupled to catheter 12 at a proximal site, and distal end 20 is coupled to member 14 at a distal site. The proximal site and distal site may be separated by a certain distance which may be varied by sliding catheter 12 relative to member 14 so that deformable members 30 become expanded or contracted. In one embodiment, the declotting apparatus may be substantially similar to that described in relation to FIG. 2A, which shows a woven basket for a deformable jacket 16. In other embodiments, the deformable members may comprise a plurality of deformable individual nitinol wires 30 (shown in FIG. 3), which may be substantially similar to the deformable wire system shown in FIGS. 1B and 1C of the present disclosure.

Rotating device 300 may comprise handle 310 attached to an outer member of a declotting apparatus, such as catheter 12. If catheter 12 and inner member 14 are allowed to move/slide on each other freely, in one embodiment catheter 12 is secured to handle 310. Activation of handle 310 pushes catheter 12 relative to inner member 14 and consequently proximal end 18 will move toward distal end 20 and arcuate the deformable wires 30. In one embodiment, rotating device 300 may comprise and/or be coupled to hand grip 312, rotational spring 315, lateral spring 317, pivot 316, attachment site 318, pinion 324, and rack 326. Handle 310 may have or be coupled to a rotational system/agent and a lateral system/agent. Handle 310 may comprise hand grip 312, one-arm lever 313, and fixed member 314. In this embodiment, catheter 12 may rotate more or less (such as between 90-120 degrees of rotation) in either a clockwise or counter clockwise direction while the inner member remains constant. In particular, only the catheter 12 and the attached proximal end of basket/jacket 18 takes part in the rotation, combined with limited axial back-and-forth movements.

In operation, pressing hand grip 310 will activate both rotational and axial mechanisms simultaneously. Rotational movement operates similar to the embodiment of FIG. 2A, such that when the operator repeatedly presses and releases hand grip 312 repeatedly, the pinion and rack will cause a back-and-forth (or clockwise and counterclockwise) 180-degree rotation (preferably less) on catheter 12. Rotational spring 315 causes the handle assembly to retract when pressure is released, thereby rotating the catheter in an opposite direction. Similarly, pressing hand grip 312 causes one-arm lever 313 to rotate about around pivot point 316 and move catheter 12 distally. Lateral spring 317 causes the handle assembly to retract when pressure is released, thereby moving the catheter proximally. Lever 313 may be coupled to catheter 12 at attachment point 318, thereby locking the lateral movement of the catheter with movement of the one-arm lever 313. In that embodiment, axial movement of member 12 (catheter) will move on member 14 proximally, thereby resulting in bowing the plurality of deformable members/wires 30 and increasing the diameter of the virtual basket and stretching them completely into a fully retracted state. Simultaneously, the proximal end of wires 30 will rotate counterclockwise in relation of the distal ends of wires 30. This simultaneous, combined proximal-distal and back-and-forth rotation movement accomplishes better and faster clot maceration than just rotational movement. In one embodiment, a portion of handle assembly 310 or any suitable alternative structure may be equipped with a lock mechanism that secures any possible position of catheter 12 relative to member 14 either continuously or at predetermined increments. Therefore, axial/lateral movements are not created and not utilized in that setting.

Although a one-arm lever and hand grip is utilized in the embodiments shown in FIGS. 2A and 3, those having skill in the art will understand, with the benefit of the present disclosure, that the rotational devices and/or handle assemblies may be configured in any number of suitable alternative manners consistent with the present disclosure and to achieve the rotation results described herein.

Figure 4:
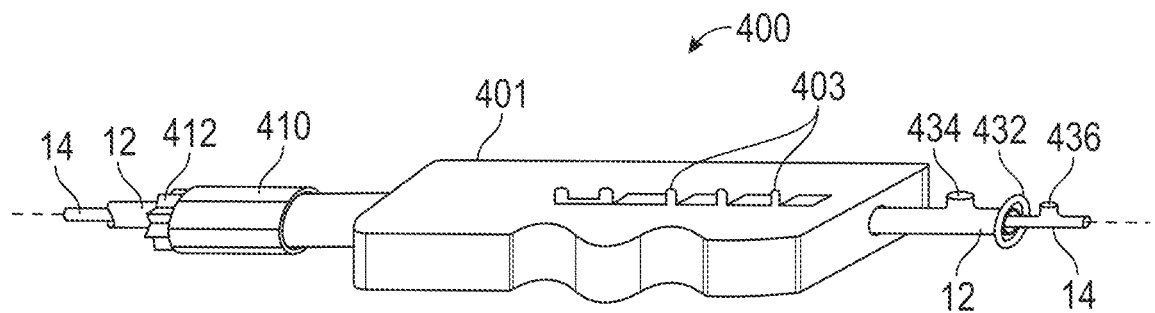
FIG. 4 illustrates one schematic of a rotational device for a declotting apparatus according to another embodiment of the present disclosure.

FIG. 4 illustrates one schematic of a rotational device for a declotting apparatus according to another embodiment of the present disclosure. The embodiment described in relation to FIG. 4 adds a low RPM motor to a conventional declotting apparatus, such as any one of the apparatuses disclosed in U.S. Pat. No. 6,146,396.

FIG. 4 shows rotational device 400 attached to a portion of a declotting apparatus (not shown) with inner member 14 and outer member 12. In one embodiment, rotational device 400 has housing 401 in which a low RPM motor (not shown) is placed. The motor may be battery driven featuring an adjustable RPM setting that can be set with separate tabs 403. For example, the selected RPM may be between 30 and 240 with 30 RPM increments (30, 60, 90, 120, 150, 180, 210, 240). Alternatively, the RPM may be selected as 30, 60, 120, 240. Other variations are of course possible. This range of rotation may be efficacious in intensive clot maceration without causing injury to the native vein. For artificial graft treatment, the upper half of the recommended RPM range (such as between 120-240 RPM) can be used without injuring the graft. In another embodiment, the motor's settings allow for alternate clockwise and counterclockwise rotations.

In one embodiment, at the distal end of motor housing 401, a coupling device 410 is configured to accept and/or couple to cogwheel 412 that is rigidly attached to outer member 12. Rotation of coupling device 410 (by the electric motor) causes cogwheel 412 to rotate, thereby causing outer member 12 to rotate. In one embodiment, rotational device 400 is located distal of locking mechanism 432, port 434, and port 436, each of which may be substantially similar to the equivalent components described in relation to FIG. 2A.

Figure 5A:
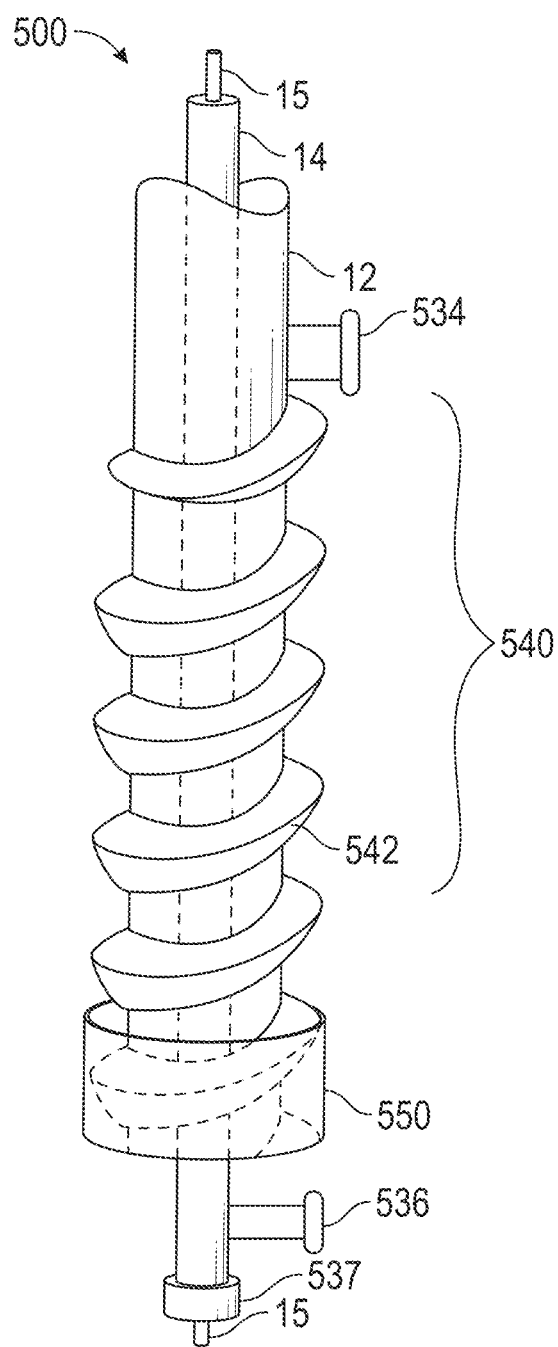
FIGS. 5A and 5B illustrate one embodiment of a locking mechanism for the disclosed rotating declotting apparatus.
Figure 5B:
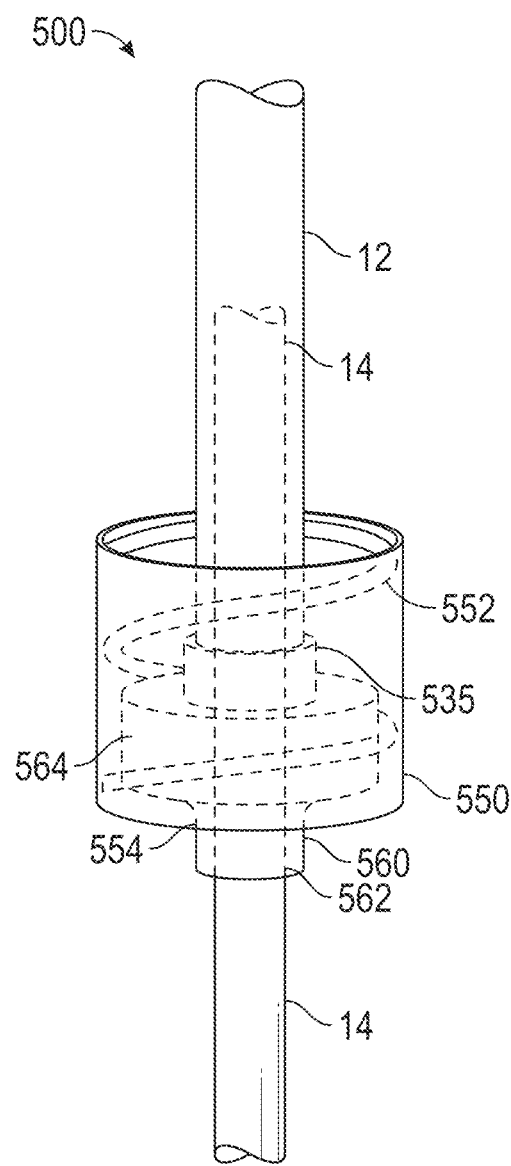

Various locking mechanisms have been described herein to the spatial relationship between catheter 12 and inner member 14. While these may be used for a rotatable declotting apparatus as described herein (see, e.g., FIGS. 2A and 3), they may also be applied to conventional declotting apparatuses that may not rotate (see, e.g., FIGS. 1A-1C and/or the apparatuses disclosed in U.S. Pat. No. 6,146,396). For example, FIGS. 5A and 5B illustrates a screw locking mechanism 500 that may be used for a conventional declotting apparatus or a rotatable declotting apparatus as described herein. FIG. 5A shows a portion of locking system 500 with a portion of a screw cap removed and FIG. 5B shows an enlarged portion of FIG. 5A illustrating the potential inside mechanism of the locking system. In one embodiment, screw mechanism 500 may be coupled to both to catheter 12 and inner member 14. For example, a proximal end of both catheter 12 and inner member 14 may each comprise and/or be coupled to a portion of screw mechanism 500. In one embodiment, a first portion of screw mechanism may comprise screw cap 550 and be coupled to inner member 14, while a second portion of screw mechanism may comprise threaded section 540 and be coupled to outer member 12.

Referring to FIG. 5A, an outer portion of catheter 12 may comprise and/or be coupled to one or more threads 542 that form threaded segment 540. In one embodiment, threaded segment 540 may comprise a single screw thread 542. Referring to FIG. 5B, screw cap 550 may be permanently connected to a proximal end of inner member 14 by a variety of attachment mechanisms. In one embodiment, screw cap 550 is coupled to inner member 14 by proximal piece 560 by using adhesive or glue 562 or another securing attachment (such as a screw or similar fastener). In some embodiments, proximal holding piece 560 may be separate from screw cap 550, and in other embodiments proximal holding piece 560 may be part of screw cap 550. Proximal portion piece 560 may be formed in such a way to prevent screw cap 550 from sliding back proximally. In one embodiment, screw cap 550 has a proximal opening 554 with a smaller diameter than an internal cavity of the screw cap such that it fits over flared portions 564 of proximal holding piece 560. In other words, a portion of proximal holding piece 560 sits within a cavity and/or internal section of screw cap 550 in an interlocking arrangement such that fixed proximal holding piece 560 holds screw cap 550 relative to inner member 14. In one embodiment screw cap 550 freely moves around proximal piece 560 and inner member 14. Screw cap 550 may include inner threading 552, and in one embodiment inner threading 552 is operably coupled to threaded portion 540. Thus, screw cap 550 may be driven up and/or down on corresponding threaded segment 540 that is permanently attached to catheter 12. In one embodiment, screw mechanism 500 not only fixes catheter 12 and inner member 14 together, it also makes it possible to adjust the spatial relationship between the two members resulting in a continuously increasing/decreasing diameter of the basket/jacket 16 and/or related deformable members 30. In one embodiment, the declotter may be expanded, or "activated," by rotating the screw cap. As a result, the working profile of the coupled declotter may increase in diameter. Using such an embodiment, one may achieve a series of controllable, different sizes of the working profile of the declotter apparatus. More specifically, deformable jacket 16, of for instance, FIG. 1, or plurality of deformable members 30 of, for instance, FIG. 3, may be fixed in place so that a desirable diameter may be easily maintained.

As shown in FIG. 5A, the declotting apparatus may comprise valves and ports on the inner and outer members similar to that shown in FIG. 2A. For example, catheter 12 may comprise side port 534 and valve 535 (see FIG. 5B), and inner member 14 may comprise side port 536 and valve 537. In one embodiment, locking system 500 may be substantially located between outer member side port 534 and inner member side port 536. In one embodiment valve 535 is located within screw cap 550 and abuts proximal holding piece 560 (see FIG. 5B). These ports and valves are used for accessing the flow areas of the inner and outer members, such as to flush the catheter with saline to remove air and blood and prevent intra-catheter coagulation.

In another embodiment to secure the spatial relationship between catheter 12 and inner member 14, the locking mechanism may comprise a ring locking mechanism 600, as shown in FIGS. 6A and 6B. FIG. 6A illustrates a view of ring locking mechanism 600 coupled to a conventional declotting apparatus or a rotating declotting apparatus as disclosed herein. FIG. 6B illustrates an enlarged view of the ring mechanism from FIG. 6A. In one embodiment, ring locking mechanism 600 comprises ring 601 that is coupled to first arm 611 and second arm 621. Each arm may have a claw 613, 623 or other attaching mechanism for rigidly attaching and/or locking with ridges, threads, or cogs 604 on cylindrical sheath 603. Cylindrical sheath 603 may be rigidly secured to an outer portion of catheter 12 such that it does not move (such as by a screw, fastener, or adhesive) or it may be arranged to axially slide a predetermined amount. In other embodiments, an outer portion of catheter 12 is coupled to and/or comprises cogs 604. There may be a plurality of cogs 604 arranged on different axial lengths or portions of cylindrical sheath 603. Each cog may be located around the entire circumference of the sheath or just a portion of the circumference (such as opposing sides of the cylindrical sheath). Ring 601 may be secured to inner member 14 by a wide variety of attachment mechanisms. In one embodiment, ring 601 is secured inner member 14 by a screw or other fastener 602.

In one embodiment, ring 601 comprises hole 604 that interfaces with corresponding holes on arms 611, 621; each of the arm holes are located on proximal portions 612 and 622 of arms 611 and 621, respectively. The holes are positioned so that all the three holes (one on each arm 611, 621 and one on ring 601) can overlap each other and arranged to accept an appropriately sized screw or fastener 602. Screw 602 is used to hold the arms in position and also to fix them to ring 601 and thereby to inner member 14. In operation, as inner member 14 is moved distally, claws 613 and 623 engage with the selected cogs of cog 604 on the cylindrical piece attached to catheter 12. Similar to locking system 500, ring locking system 600 allows the spatial relationship between catheter 12 and inner member 14 to be adjusted and therefore the length/diameter of the working profile of the deformable basket/jacket of the declotting apparatus. In one embodiment, arms 611, 621 may be fixed at certain points (such as cogs 604) so as to lock the ring in a fixed position, and consequently the diameter of the declotter apparatus, in place. Similar to the embodiment shown in FIG. 5A, one may achieve a series of controllable, different sizes of the working profile of the declotter apparatus. More specifically, deformable jacket 16, of for instance, FIG. 1, or plurality of deformable members 30 of, for instance, FIG. 3 may be fixed in place so that a desirable diameter may be easily maintained.

Similar to FIG. 5A, the declotting apparatus illustrated in FIG. 6A may comprise valves and ports on the inner and outer members. For example, catheter 12 may comprise side port 634 and valve 635, and inner member 14 may comprise side port 636 and valve 637. In one embodiment, locking system 600 may be substantially located between outer member side port 634 and inner member side port 636.

One of skill in the art will realize that many other rotational systems are also possible to rotate one or both of inner and outer members 12 and 14. For example, the rotational system may be any ratchet mechanism that allows for repeat rotations in the same direction, or a barrel cam mechanism with a lever or rack. The rotational system may be coupled to the declotting apparatus (or a portion thereof) in a variety of ways to rotate one or both of inner and outer members. FIGS. 7-10 show various additional embodiments of a rotational system in addition to those described in FIGS. 2A, 3, and 4. One of skill in the art will recognize that others are also possible within the scope of this disclosure.

Figure 7:
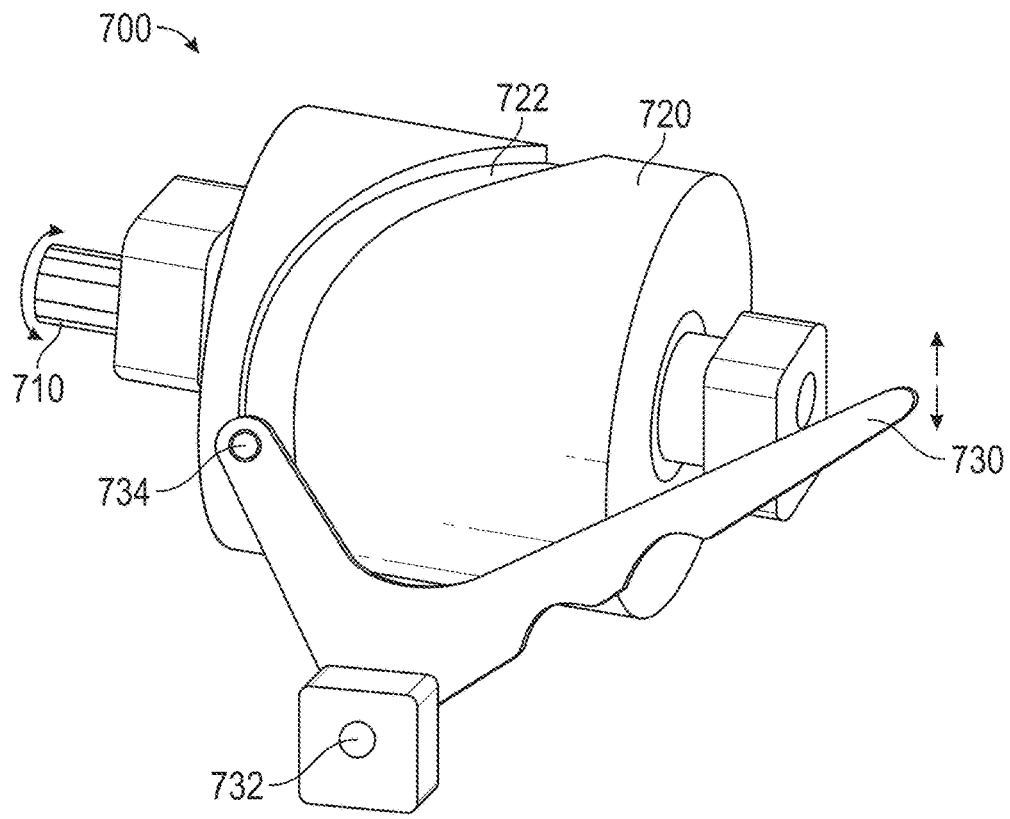
FIG. 7 illustrates one embodiment of a rotation mechanism for the disclosed declotting apparatus.

FIG. 7 illustrates one embodiment of rotational system 700 that utilizes a barrel cam mechanism with a lever. In one embodiment, rotation system 700 consists of cylindrical element 720 with a helically arranged groove 722 on an exterior portion of the cylindrical element. Rotation system 700 also comprises lever 730 coupled to cylindrical element 720 by pivot 732. In one embodiment, lever 730 comprises a distal end with a follower 734 (such as a shaft or pin) that is arranged to move within groove 722. Rotating element 710 is coupled to one end of cylindrical element 720, and the other end of the rotating element may be coupled to a declotting apparatus (not shown). Movement and/or actuation of lever 730 (such as up and down motion) causes the cylindrical element to rotate, thereby causing rotating element 710 to rotate the declotting apparatus.

Figure 8:
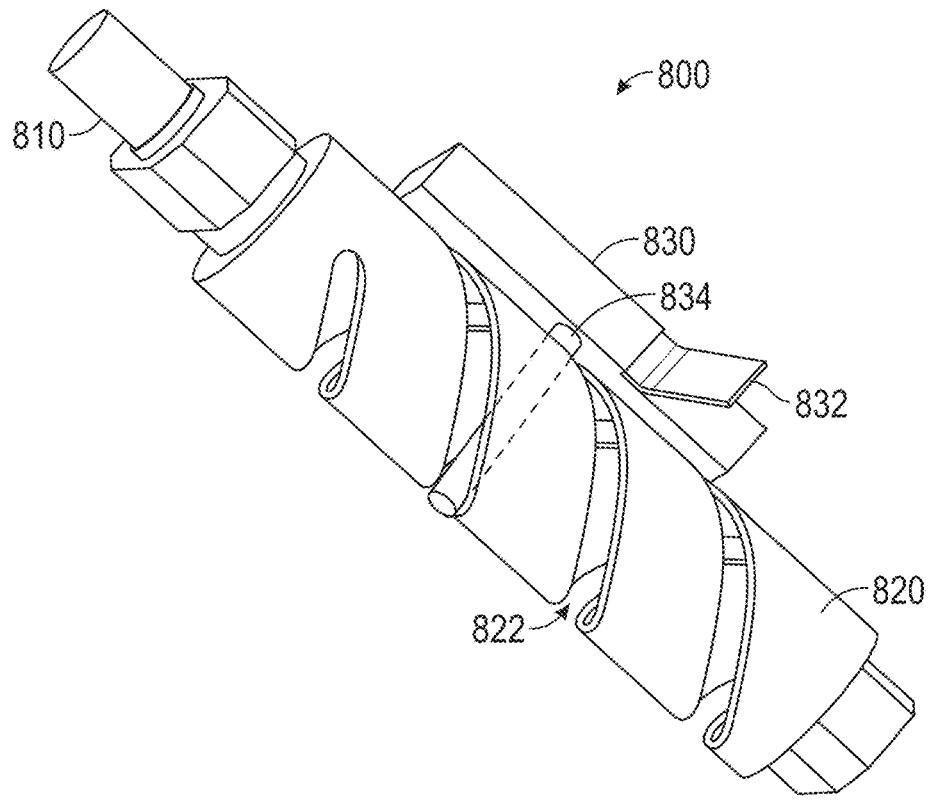
FIG. 8 illustrates one embodiment of a rotation mechanism for the disclosed declotting apparatus.

FIG. 8 illustrates one embodiment of rotational system 800 that utilizes a barrel cam mechanism with a rack. In one embodiment, rotation system 800 consists of cylindrical element 820 with helically arranged groove 822 located on an exterior portion of the cylindrical element. Rotation system 800 also comprises sliding element 830 coupled to cylindrical element 820. In one embodiment, sliding element 830 acts as a rack system and comprises and/or is coupled to follower 834 (such a shaft or pin) that is arranged to move within groove 822 as the cylindrical element 820 rotates. Sliding element 830 may also comprise knob or thumb-push button 832 for easier movement of the sliding element. Rotating element 810 is coupled to one end of cylindrical element 820, and the other end of the rotating element may be coupled to a declotting apparatus (not shown). Movement and/or actuation of the sliding element in an axial direction (e.g., a back and forth movement) causes the follower to move along the groove and the cylindrical element to rotate, thereby causing rotating element 810 to rotate the declotting apparatus.

Figure 9:
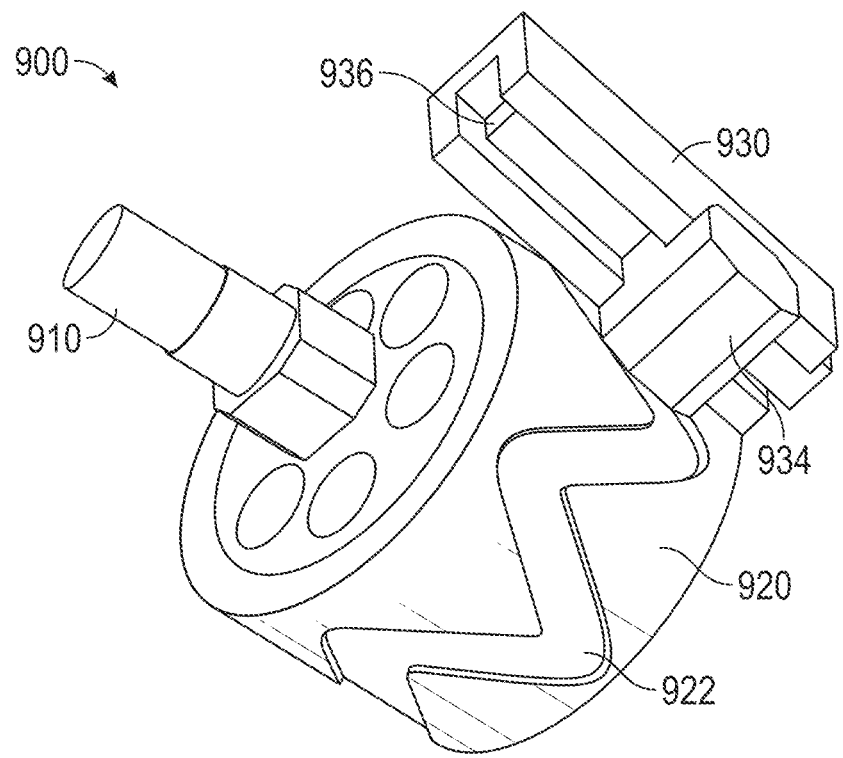
FIG. 9 illustrates one embodiment of a rotation mechanism for the disclosed declotting apparatus.

FIG. 9 illustrates one embodiment of rotational system 900 that utilizes a barrel cam mechanism with a sliding element. In one embodiment, rotation system 900 consists of cylindrical element 920 with a continuous groove 922 on an exterior portion of the cylindrical element. Groove 922 may be a zig-zagged groove (as shown in FIG. 9) or a sinusoidal shaped groove. Rotation system 900 also comprises sliding element 930 coupled to cylindrical element 920. In one embodiment, sliding element 930 is coupled to follower 934 that is arranged to move within groove 922 as the cylindrical element 920 rotates. Sliding element 930 may also comprise groove 936 in which a corresponding tooth or protrusion of follower 934 moves within. A rotating element 910 is coupled to one end of cylindrical element 920, and the other end of the rotating element may be coupled to a declotting apparatus (not shown). Movement and/or actuation of follower 934 in an axial direction (e.g., a back and forth movement) causes the follower to move along the groove and the cylindrical element to rotate, thereby causing rotating element 910 to rotate the declotting apparatus.

Figure 10:
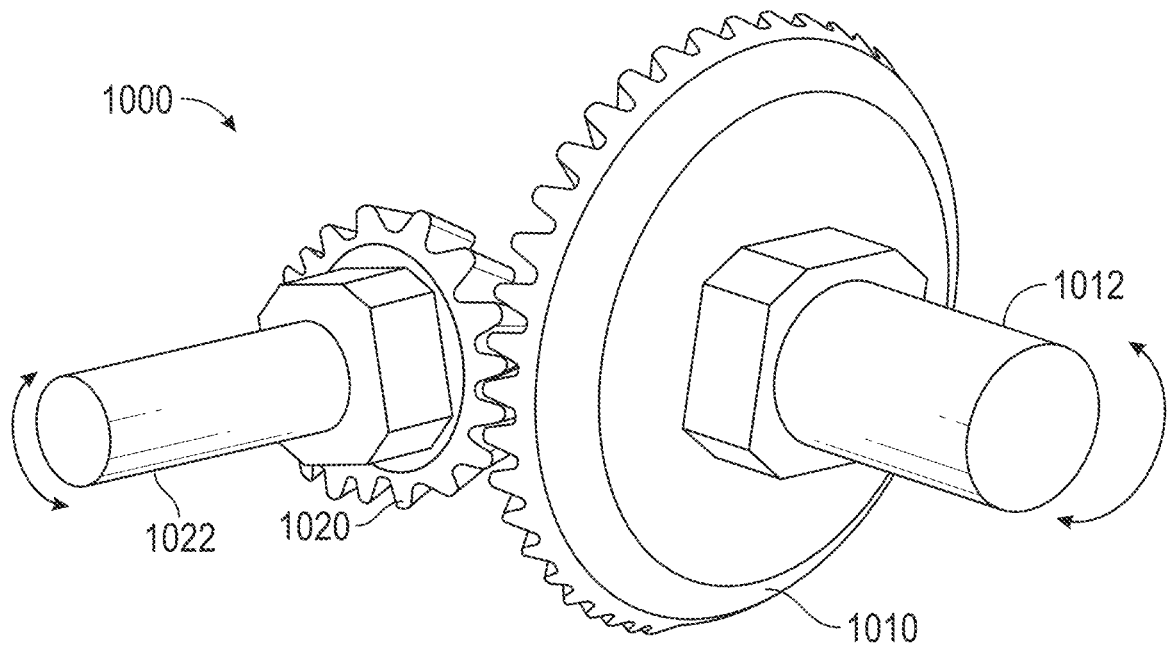
FIG. 10 illustrates one embodiment of a rotation mechanism for the disclosed declotting apparatus.

FIG. 10 illustrates one embodiment of rotational system 1000 that utilizes a plurality of gears. In one embodiment, rotation system 1000 consists of first driven gear 1010 coupled to first rotating piece 1012 and second gear driven 1020 coupled to second rotating piece 1022. In one embodiment, the first gear is arranged at a predetermined angle to the second gear. For example, first gear 1010 may be substantially perpendicular to second gear 1020. In one embodiment, rotating piece 1012 is coupled to a lever, arm, or other actuating device (not shown) that, when actuated, causes movement of driven gear 1010. Movement of first driven gear 1010 in a first direction (e.g., clockwise) causes movement of second driven gear 1020 in a second direction (e.g., counter clockwise). Rotating piece 1022 may be coupled to a declotting apparatus (not shown). The gears may be arranged to produce different rotational movements or gear ratios based on the sizes of the diameters of the gears. For example, every rotation of gear 1010 may cause two rotations of gear 1020 (or vice versa). The particular arrangement and sizing of the gears is based on the intended rotational speed and control of the declotting apparatus.

Figure 11B:
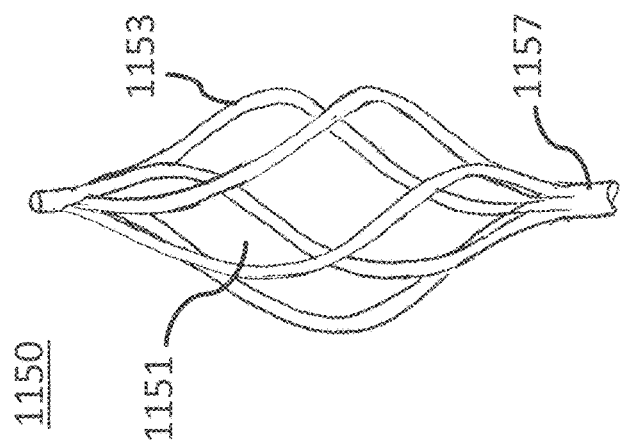
FIGS. 11A and 11B illustrates various schematics of a rotational device for a declotting apparatus according to one embodiment of the present disclosure.
Figure 11A:
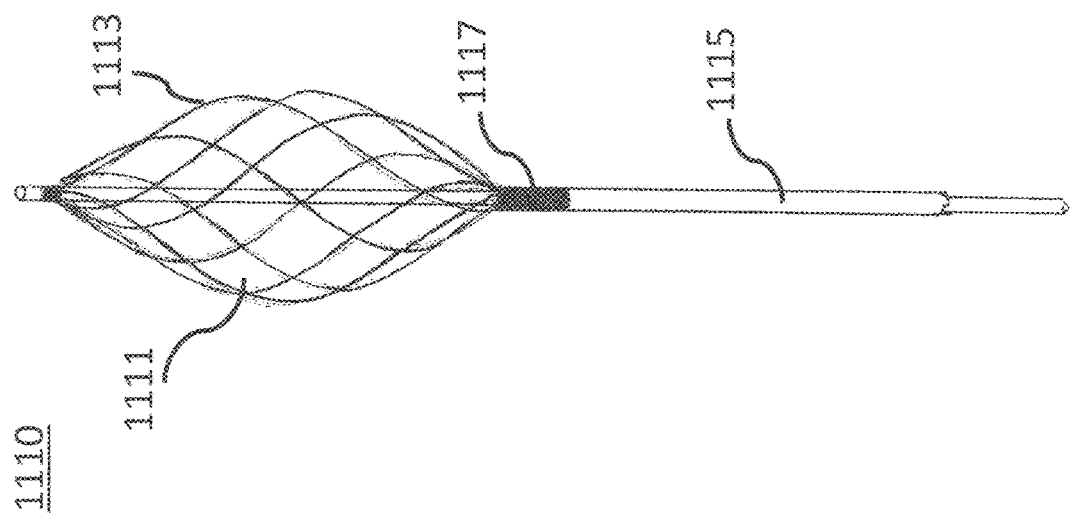

FIGS. 11A and 11B illustrate alternative embodiments of a basket of the disclosed declotting apparatus. In one embodiment, the baskets of FIGS. 11A and 11B may be similar to basket 16 of FIG. 2A (and utilized in the same manner) but are formed of a plurality of wires to form a substantially helically shaped basket. FIG. 11A shows helical basket 1110 formed of eight wires 1113, while FIG. 11B shows helical basket 1150 formed of five wires 1153. Each of the wires in helical baskets 1110, 1150 may comprise shape memory material, such as superelastic nitinol wires. Pockets and/or gaps 1111, 1151 may be formed between the wires. The diameter of the baskets is adjustable based on the protrusion of the basket from the catheter (such as catheter 1115 in FIG. 11A). Like basket 16 in FIG. 2A, each of the helical baskets has a proximal end and a distal end. The proximal end of the basket is coupled to the catheter at a proximal site, and the distal end of the basket is coupled to an inner member at a distal site. The proximal site and distal site of the basket may be separated by a certain distance which may be varied by sliding catheter 1115 relative to the member so that the helical basket becomes expanded or contracted. Rings 1117 and 1157 couple and/or otherwise hold wires 1113, 1153, respectively, in place. Each of the deformable wires 1113, 1153 may be twisted over the remaining wires to form a helical structure. The helical basket disclosed in FIGS. 11A and 11B is advantageous because the increased number of wires makes a larger contact surface for more efficacious clot maceration; in contrast, FIGS. 1B and 1C show the prior art declotting apparatuses in which the wires are substantially parallel to the longitudinal axis of the catheter and the wires become buckled only when the two ends of the wires are pushed to each other.

In one embodiment, each of the wires utilized in the basket for the disclosed declotting apparatus (see, e.g., basket 16 in FIG. 2A, deformable members 30 in FIG. 3, baskets 1110 and 1150 in FIGS. 11A and 11B) is formed of a traditional shape memory wire, such as a single wire made of nitinol. As is known in the art, the deformable members can be programmed by heat treatment into preformed shapes. In particular, they may be programmed to substantially recover an arcuate shape upon removal of a compressing force. Programming of superelasticity or thermal memory may be accomplished by any one of a number of techniques known in the art, such as by first forming a desired arcuate shape. In a further possible embodiment, the deformable members are made of platinum cored microtubes. The platinum content increases the radiopacity of the device that in turn increases its visibility under fluoroscopy (X-ray) during the procedure. Better visibility translates to safety, efficacy and speediness of the procedure.

In other embodiments, the wire may be formed of a bundled wire (e.g., a set of individual wires coupled together) instead of a single wire. The bundle of wires may comprise different sized wires and/or wires of different materials. In one embodiment, rather than using a single filament or wire strand, a wire rope and/or wire bundle may be formed of a plurality of individual wire strands that are coupled together. The bundled wire may contain one or more nitinol microtubing(s) with one or more platinum wires. Each of these wire bundles may be used to form a wire for the deformable basket and/or jacket.

A bundle of wires instead of a single wire provides numerous benefits. For example, if one of the plurality of wires fails, the other wires can easily take up the load. Thus, any flaws in an individual wire is not as critical as compared to looking at the bundle of wires as a whole. A bundle of wires also prevents fatigue of the single individual wire, similar to the principle of rope wires (which use braided strands of individual rope filaments). As another benefit, a bundled wire provides increased tensile strength while the wire diameter can be reduced. The reduction of the wire size allows for reducing the overall dimensions/size of the device. This is important when the device is used in a small vessel, which requires smaller caliber devices. The reduction of the size of the wire can also lead more favorable physical properties. For example, a bundled wire provides for increased radiopacity of the wire; the wire bundle can contain platinum cored nitinol microtubings that significantly enhance the visibility of the devices on fluoroscopy. Better visibility enhances the speed, efficacy, and safety of the procedure. Further, faster removal of the foreign body translates to less radiation to the patients and the personnel.

There are numerous design variations of a wire bundle that can be used in the disclosed deformable jacket/basket depending on the intended basket design, application of the declotting device, and anatomical location in which the declotting apparatus is to be deployed. For example, some of the wires may be different shapes and/or sizes, while some of the wires may be different materials. Following the principle of the wire rope, virtually endless variations of a wire bundle can be created that can be used as individual wire strands for a loop of the disclosed declotting device.

FIGS. 12A-12E illustrate various schematics of wire bundles according to one embodiment of the present disclosure.

FIG. 12A illustrates wire bundle 1200, which may be formed of seven individual wire strands 1203. Each of these strands may be twisted together helically. In one embodiment, one of the wires may comprise a nitinol microtube that may contain a platinum core used as a radiopaque marker, which is used to increase the visibility of the wires on fluoroscopy (X-ray) during use. For example, central wire 1201 may comprise a microtube with a platinum core. In other embodiments, some or all of the wires may contain microtubings with platinum cores. The sizes of the wires 1203 may be the same or different. For example, each of the seven individual wires 1203 may have an approximately 0.003" diameter (d), resulting in an overall diameter (D) of wire bundle 1200 of approximately 0.009". In another embodiment, one or more of the individual wires itself may comprise a plurality of smaller individual wires, thereby creating a more complex but stronger wire bundle (again, much like a braided rope). In one embodiment, one or more of wires 1203 may comprise at least three wires, which each may comprise a diameter of 0.001" thereby keeping the overall diameter of wire 1203 at approximately 0.003". Of course, other diameters and sizes of wires may be utilized as would be known to one of ordinary skill in the art based on the present disclosure.

FIG. 12B illustrates another schematic of a wire bundle according to one embodiment of the present disclosure. Wire bundle 1210 may be substantially similar to wire bundle 1200 but comprises one or more wires that are flattened, non-symmetrical, and/or non-cylindrical. For example, core wire 1211 (which may or may not be compacted) may be surrounded by a plurality of flattened wires 1213 that are not cylindrical, thereby providing an overall compacted shape of wire bundle 1210. Among other benefits, a compacted wire bundle provides the same amount of wire with an overall less diameter than if each of the wires was not compacted. The overall amount of wire material and strength remains substantially the same between the different bundles between FIGS. 12A (non-compacted) and 12B (compacted).

FIG. 12C illustrates another schematic of a wire bundle according to one embodiment of the present disclosure. Wire bundle 1220 may be substantially similar to wire bundle 1200 but comprises additional wires. For example, wire bundle 1220 may comprise center wire 1221, a second set of wires 1223 (such as six wires) surrounding the center wire, and a third set of wires 1225 (such as twelve wires) surrounding second set of wires 1223. In the embodiment illustrated in FIG. 12C, there are approximately 19 individual wires, each of which may be further comprised of individual wires. Again, this embodiment is similar to wire bundle 1200 but adds an outer peripheral set of wires 1225.

As illustrated above, FIG. 12B illustrates a compacted wire, in which some of the individual wires are shaped to minimize the dead space within a wire bundle which exists when each of the wires are cylindrical/symmetrical. Similarly, FIG. 12D illustrates a compacted wire bundle version. Compacted wire bundle 1230 comprise center wire 1231, a second set of wires 1233 (such as nine wires) surrounding the center wire, and a third set of wires 1235 (such as nine wires) surrounding the second set of wires 1233. The outer set of wires 1235 comprises compacted and/or non-symmetrical wires, which reduces the overall diameter of the wire bundle 1230 if all of the wires had been symmetrical. As illustrated, the second set of wires 1233 has a diameter less than a diameter of the center wire and the third set of wires.

FIG. 12E illustrates another schematic of a wire bundle according to one embodiment of the present disclosure. Wire bundle 1240 may be substantially similar to wire bundle 1220 (FIG. 12C) but comprises additional wires. For example, like bundle 1220, wire bundle 1240 may comprise center wire 1241, a second set of wires 1243 (such as six wires) surrounding the center wire, and a third set of wires 1245 (such as twelve wires) surrounding the second set of wires 1243. However, bundle 1240 also includes wires 1247 (such as six wires) between the outer set of wires 1245 and the second set of wires 1243. Wires 1247 may have a diameter substantially smaller than a diameter of the other wires. In one embodiment, the outer set of wires 1245 microtubings with platinum cores. In other embodiments, smaller wires 1247 may comprise platinum instead of the outer set of wires.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Many other variations in the system are within the scope of the invention. For example, the rotating device may or may not allow for sliding and/or lateral movement of a portion of a declotting apparatus. The declotting apparatus may comprise one or more bendable wires, such as a plurality of deformable members, or a single basket like shape. The deformable members may be a shape memory material such as nitinol. Other shapes and configurations of the rotating wire mechanism is possible. Any of the wires disclosed herein (such as those for the deformable basket/jacket) may be a single wire or a plurality of wires, such as a wire bundle. A wire bundle may be a twisted and/or helical wire bundle. Any one or more of the wires utilized in a wire or wire bundle may have platinum or some other marker to provide increased radiopacity, such as nitinol microtubings with a platinum core. It is emphasized that the foregoing embodiments are only examples of the very many different structural and material configurations that are possible within the scope of the present invention.

Although the invention(s) is/are described herein with reference to specific embodiments, various modifications and changes can be made without departing from the scope of the present invention(s), as presently set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

What is claimed is:

1. A declotting apparatus, comprising:
    an outer member;
    an inner member positioned within the outer member, wherein the inner member is configured to be fixed in position relative to the outer member;
    a plurality of deformable members coupled to the inner member and the outer member; and
    a rotational device configured to rotate the outer member, wherein the rotational device comprises
        a grip body that comprises a handle;
        a spring coupled to the grip body; and
        a gear mechanism coupled to the grip body and the outer member, wherein the gear mechanism is a rack and pinion located between two portions of the handle,
    wherein the handle is configured to move between a first position and a second position that causes rotation of the outer member relative to the inner member.

2. The apparatus of claim 1, wherein the outer member is a catheter.

3. The apparatus of claim 2, further comprising a guidewire positioned within the inner member and extending through a distal site of the catheter.

4. The apparatus of claim 1, wherein the plurality of deformable members comprise a proximal portion and a distal portion, said proximal portion being coupled to the outer member at a proximal site and said distal portion being coupled to the inner member at a distal site.

5. The apparatus of claim 1, wherein the plurality of deformable members comprise nitinol wire.

6. The apparatus of claim 1, wherein the plurality of deformable members are elastically deformable.

7. The apparatus of claim 1, wherein the plurality of deformable members form a helical structure.

8. The apparatus of claim 1, wherein each of the plurality of deformable members comprise a wire bundle.

9. The apparatus of claim 1, wherein at least some of the plurality of deformable members comprise a wire bundle.

10. The apparatus of claim 1, wherein the rotational device is coupled to the outer member.

11. The apparatus of claim 1, wherein the rotational device is coupled to the inner member.

12. The apparatus of claim 1, wherein the rotational device is configured to rotate the outer member and the inner member when the inner member is positionally fixed to the outer member.

13. The apparatus of claim 1, further comprising a locking mechanism that holds the inner member in position relative to a position of the outer member.

14. The apparatus of claim 13, wherein the locking mechanism is configured to move the inner member and outer member between a plurality of fixed positions.

15. The apparatus of claim 1, wherein the rotational device is detachably coupled to the inner and outer members.

16. A declotting apparatus, comprising:
    an outer member;
    an inner member positioned within the outer member;
    a plurality of deformable members coupled to the inner member and the outer member; and
    a rotational device configured to rotate the outer member or inner member,
    wherein the rotational device comprises
        a grip body that comprises a handle;
        a spring coupled to the grip body; and
        a gear mechanism coupled to the grip body and the outer member, wherein the gear mechanism is a rack and pinion located between two portions of the handle, wherein the rotational device is detachably coupled to the inner and outer members.

17. The apparatus of claim 16, wherein the inner member is fixed in position relative to the outer member.

18. The apparatus of claim 16, wherein the inner member and outer member are coupled such that rotation of the outer member causes rotation of the inner member.

19. A rotational device for a declotting apparatus, comprising:
a handle assembly configured to couple to a declotting apparatus, wherein the declotting apparatus comprises a catheter and an inner member, wherein the handle assembly comprises two portions;
a spring coupled to the two portions of the handle assembly; and
a gear mechanism coupled to the handle assembly and catheter, wherein the gear mechanism is a rack and pinion located between the two portions of the handle assembly,
wherein the handle assembly is configured to actuate the gear mechanism to rotate the catheter relative to the inner member,
wherein the handle assembly is configured to move between a first position and a second position that causes rotation of the catheter relative to the inner member.

20. The device of claim 19, further comprising a plurality of deformable members coupled to the inner member and catheter, wherein actuation of the handle assembly is configured to rotate the plurality of deformable members.

21. A method for declotting a vascular site, comprising
providing a declotter, wherein the declotter comprises
a catheter;
a member positioned within the catheter;
a plurality of deformable members coupled to the catheter and the member; and
a handle mechanism, wherein the handle mechanism comprises
a first handle portion comprising a grip body;
a second handle portion;
a spring coupled to the first handle portion and the second handle portion; and
a gear mechanism coupled to the grip body and the member;
wherein the gear mechanism is a rack and pinion located between the first handle portion and the second handle portion;
positioning the declotter adjacent said site;
rotating the plurality of deformable members to declot said vascular site; and
actuating the handle mechanism to rotate the plurality of deformable members,
wherein actuation of the handle mechanism rotates the catheter relative to the member.

22. The method of claim 21, wherein actuation of the handle mechanism operatively couples the rack with the pinion.

23. The method of claim 21, wherein the plurality of deformable members having a proximal portion and a distal portion, said proximal portion being coupled to the catheter at a proximal site and said distal portion being coupled to the member at a distal site; said proximal site and said distal site being separated by a distance.

24. The method of claim 21,
wherein the declotter further comprises an injection port and one or more injectors coupled to the catheter, and further comprises injecting contrast through the declotter with said injection port.

25. The method of claim 24, further comprising injecting thrombolytic agents through the declotter with said injection port.

26. The method of claim 21, wherein said vascular site is a thrombosed hemodialysis access graft site.

27. The method of claim 21, wherein said vascular site is a thrombosed intragraft site.

28. The method of claim 21, wherein said vascular site is a venous stenosis site.

29. The method of claim 21, wherein said vascular site is a large vein that comprises a massive thrombosis.

\* \* \* \* \*